(12) United States Patent
Gerding

(10) Patent No.: US 6,635,260 B1
(45) Date of Patent: Oct. 21, 2003

(54) **METHODS AND COMPOSITIONS FOR PREVENTION AND TREATMENT OF *CLOSTRIDIUM DIFFICILE*-ASSOCIATED DISEASES**

(76) Inventor: Dale N. Gerding, 680 N. Lakeshore Dr., Chicago, IL (US) 60611

( * ) Notice: Subject to any disclaimer, the term of this patent is extended or adjusted under 35 U.S.C. 154(b) by 0 days.

(21) Appl. No.: 09/386,464

(22) Filed: Aug. 9, 1999

Related U.S. Application Data

(63) Continuation of application No. PCT/US96/14868, filed on Sep. 13, 1996.
(60) Provisional application No. 60/003,847, filed on Sep. 15, 1995.

(51) Int. Cl.[7] .................. A61K 38/00; A61K 39/02; A61K 39/08; C12Q 1/24; C12Q 1/04; C12N 3/00
(52) U.S. Cl. ............. 424/247.1; 424/114; 424/234.1; 424/239.1; 435/30; 435/34; 435/342
(58) Field of Search .................. 424/114, 234.1, 424/239.1, 247.1; 435/30, 34, 242

(56) References Cited

PUBLICATIONS

Clabots C.R., et al. (1993) "Development of a Rapid and Efficient Restriction Endonuclease Analysis Typing System for *Clostridium difficile* and Correlation with Other Typing Systems." *Journal of Clinical Microbiology* 31(7): 1870–1875.
Delmée, M. and Avesani, V. (1990).
Seal, D. et al. (1987) Treatment of Relapsing *Clostridium difficile* Diarrhoea by Administration of a Non–Toxigenic Strain. Eur J Clin Microbiol 6(1): 51–53.
Tvede, M. and Rask–Madsen, J. (1989) "Bacteriotherapy for Chronic Relapsing *Clostridium difficle* Diarrhoea in Six Patients." *The Lancet* 1(8648): 1156–1160.
Wilson, K.H. and Sheagren, J.N. (1983) "Antagonism of Toxigenic *Clostridium difficile* by Nontoxigenic c. Difficile." *The Journal of Infectious Diseases* 147(4): 733–736.
Gerding et al., "*Clostridium difficile*–Associated Diarrhea and Colitis," Infection Control and Hospital Epidemiology, Aug. '95, V. 16 No. 8.
Kristiansson et al. "Comparison of Restriction Endonuclease Analysis, Ribotyping, and Pulsed–Field Gel . . . ," J. Clin. Microbiol. Aug. '94 32:8.
Borreillo et al., "Protection of Hamsters Against *Clostridium difficle* Ileocaecitis . . . ," J. Med. Microbiol. vol. 19 (1985), 339–350.

*Primary Examiner*—James Housel
*Assistant Examiner*—Shanon Foley

(57) ABSTRACT

This invention provides methods and compositions for preventing and treating *Clostridium difficile*-associated disease in a subject, wherein the subject is either a human or non-human animal. The method comprises administering to the subject an effective amount of a non-toxigenic strain of *C. difficile* or a combination of strains. A suitable non-toxigenic strain is selected from the M, T, C, P, S and AP group as defined by restriction endonuclease analysis. Also provided are pharmaceutical compositions and unit dosage forms comprising a single strain or a combination of strains selected from a non-toxigenic *C. difficile* group and a method for selecting non-toxigenic *C. difficile* strains.

36 Claims, 3 Drawing Sheets

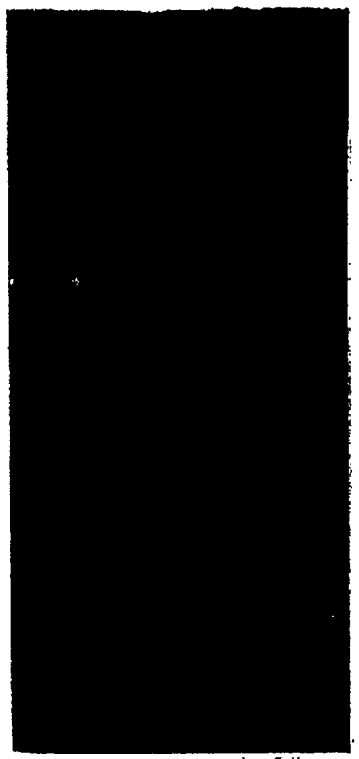 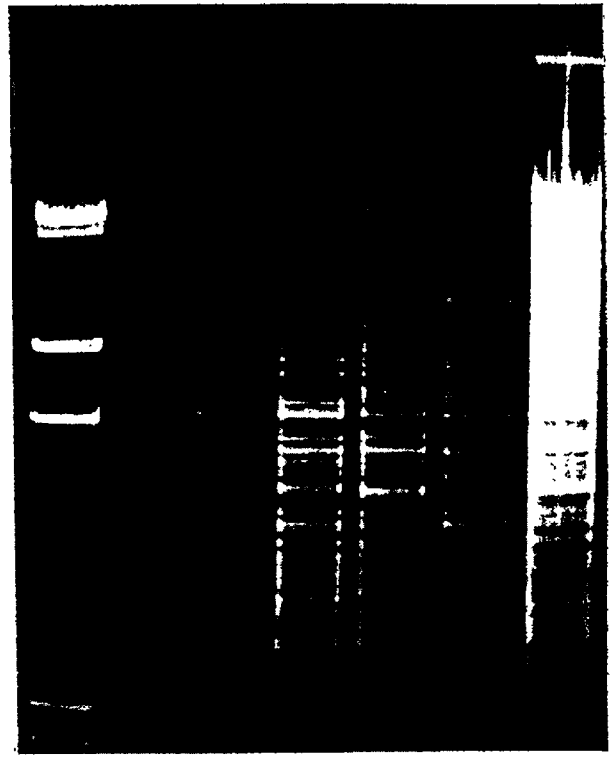
λ   S1         S1
    PLASMID
λ   M3   M4   M23   T7   J9   VPI2018
Fig. 3A
Fig. 3B

METHODS AND COMPOSITIONS FOR PREVENTION AND TREATMENT OF *CLOSTRIDIUM DIFFICILE*-ASSOCIATED DISEASES

This application is continuation of co-pending application PCT/US96/14868 with an International Filing Date of Sep. 13, 1996, and 60/003,847, filed Sep. 15, 1995 now abandoned Nov. 14, 2002.

The U.S. Government has rights in this invention pursuant to a nonexclusive, irrevocable, royalty-free license granted to the Department of Veterans Affairs on the invention in U.S. Ser. No. 60/003,847.

This invention relates to methods and compositions useful to prevent and treat *Clostridium difficile*-associated diseases.

*Clostridium difficile*-associated diseases (CDAD) are the most frequently identified causes of nosocomial diarrhea (that is, in healthcare facilities), producing both endemic and epidemic diarrhea. CDAD incidence ranges from <1% to 7.8% of hospital discharges. CDAD prolongs hospitalization, increases the costs of care, and causes considerable morbidity, especially in the 10–20% who relapse, and a mortality of 0.6–2.3%. Elderly patients and those who have long hospital stays are at particularly high risk.

Horizontal transmission of *C. difficile* in the hospital to susceptible patients receiving antibiotics accounts for the vast majority of CDAD incidence. No infection control method has been widely successful at preventing transmission, and prophylactic measures aimed at preventing symptoms if transmission occurs have proven cumbersome, ineffective, or both. Therefore, new and innovative approaches to prevent CDAD are needed.

In animals, *C. difficile*-related diseases cause great economic losses. Notably, in horse breeding, young foals are extremely susceptible, infection generally resulting in death; chinchillas are also vulnerable. Antibiotic treatment in animals is not only expensive, but is not completely effective.

There is a need for relatively inexpensive and effective prophylactic methods and treatments.

Although use of a non-toxigenic strain of *C. difficile* has been suggested as a solution, selection of strains has been random, and results ambiguous or discouraging. For example, Wilson and Sheagren (1983) report that colonization of cefotoxin-treated hamsters with a strain of *C. difficile*, said to be non-toxigenic, but not further characterized, before challenge with toxigenic *C. difficile* resulted in only 72% improvement in survival compared to controls. Even more discouraging, when toxigenic and non-toxigenic strains were given at the same time, no significant survival benefit was obtained.

Borriello and Barclay (1985) reported that prior colonization of clindamycin-treated hamsters with non-toxigenic strains of *C. difficile* protected them for at least a short time period from subsequent colonization with a toxigenic strain. The non-toxigenic strains were given designations, but were not further characterized. In total, 13 of 18 "protected" hamsters survived for up to 27 days, whereas all 27 animals challenged with the toxigenic strain alone died within 48 hours. However, even in toe "protected" animals, the toxigenic strain eventually became dominant and caused disease, and death occurred in most cases due to infection. The authors concluded that the extent to which this sort of approach may be therapeutically useful was difficult to assess.

Seal et al. (1987) reported that two patients (designated A and B) with relapsing *C. difficile* diarrhea following metronidazole and vancomycin therapy were colonized with a non-toxigenic avirulent *C. difficile* strain given orally in three doses. Patient A did not suffer a further relapse during the four months that she was studied after treatment with non-toxigenic *C. difficile*. Patient B did suffer a relapse, but it was reported as milder than previous relapses. The authors acknowledged that there was no showing that the bacteriotherapy actually prevented or mitigated relapse. Indeed, in one of the two patients, it had not prevented relapse. Obviously, conclusions on only two patients are questionable. The authors also stated that there was a need for further studies before this approach should be considered for trials in the hospital.

Corthier and Muller (1988) reported that administering a non-toxigenic strain of *C. difficile* to gnotobiotic mice from 18 hours to 10 days before challenge with toxigenic *C. difficile* resulted in 100% survival, however, the controls exhibited 60% survival in this experiment, suggesting only about 40% improvement. It cannot be determined from the article how long this level of protection persisted. The mice appear to have been observed for only eight days after administration of the toxigenic *C. difficile*.

Borriello (1988) reviewed bacteriotherapy approaches for the prevention and treatment of *C. difficile* infection of the gut, including use of whole fecal mixtures, synthetic mixtures of fecal organisms, lactobacilli, the yeast *Saccharomyces boulardii*, and non-toxigenic *C. difficile* in vitro, and in vivo in animals and in vivo in humans. He concluded that all of the bacteriotherapy approaches need to be further evaluated, but that a non-toxigenic strain of *C. difficile* may fulfill criteria for a "cleaner" and well defined preparation.

No reports of attempts to use *C. ditficile* bacteriotherapy to protect against CDAD are known since 1988. Experimental bacteriotherapy is in clinical use in the U.S. with *Saccharomyces boulardii*, a yeast, which is reported to show some benefit in reducing relapses and in preventing antibiotic-associated diarrhea, but is not effective against *C. difficile* diarrhea (McFarland et al., 1994; Surawicz et al., 1989). A problem with Saccharomyces is that twice daily administration is required for four weeks, making compliance difficult for patients.

The successful use of rectal instillation of feces and bacterial mixtures of fecal organisms to treat chronic relapsing *C. difficile* has been reported in six patients (Tvede and Rask-Madsen, 1989). Use of bacteriotherapy has not been wide-spread due to reluctance by physicians and patients aesthetically to use fecal preparations. At present, methods and compositions for specific prevention of *C. difficile* diarrhea have not been reported.

SUMMARY OF THE INVENTION

The present invention provides methods and compositions for preventing and treating CDAD (*C. difficile*-associated disease) in subjects including humans and non-human animals, e.g. mammals and birds. "Subjects" are persons or animals who have received antimicrobials o antineoplastics (which also have antimicrobial activity). For prevention of *C. difficile* disease, a composition of a selected non-toxigenic strain of *C. difficile* is administered within about 24 hrs. after antibiotic (antimicrobial) or antineoplastic agents. This is to allow time for suppression of the normal intestinal flora, but not enough time for toxigenic strains of *C. difficile* to become established in the gastrointestinal tract. Examples of types of antimicrobial agents known to cause risk of *C. difficile* disease in human and non-human animals or birds include cephalosporins, clindamycin, ampicillin, tetracyclines.

For treatment of subjects who have C. difficile disease, first antibiotics (usually vancomycin or metronidazole) must be administered that are directed to control of the disease, then—to prevent a relapse, the compositions of the present invention are administered.

The methods of the present invention comprise administering to the subject an effective amount of spores (generally in the order of $5 \times 10^5$ to $10^6$ colony-forming units) of a selected non-toxigenic strain of C. difficile. Higher or repeated doses may be required for treatment than for prevention. "Effectiveness" is determined by clinical criteria showing the risk of developing CDAD is reduced by 80% or more compared to comparably exposed patients or animals in the same environment.

An aspect of the invention is compositions for use in the method, said compositions including selected non-toxigenic strains of C. difficile. Certain non-toxigenic strains (types) of C. difficile are found to prevent disease better against specific toxigenic types of C. difficile than against other toxigenic types. Methods to select these strains are an aspect of the present invention.

A suitable non-toxigenic strain is a strain selected from the M, T, C, AP or other non-toxigenic groups as described by Clabots et al. (1993) or as genetically engineered to be non-toxigenic. These groups are selected because their relative high frequencies as isolates from persons or humans in which colonization has occurred, predicts their success as colonizers for purposes of the invention. Generally, relatively frequent groups occur in at least 5% of the non-toxigenic isolates, preferably in at least 15%; and more preferably in at least 25% of the isolates. Similarly, within a group, preferred strains are those that are most frequent. A single purified strain of the M group, or of another single group, or a combination of strains within a group or a combination of strains from different groups, are suitable. M group strains, in particular M3 and M23 are preferred singly or in combination with other strains. Also provided are pharmaceutical compositions and unit dosage forms comprising a strain selected from the non-toxigenic C. difficile groups, or a combination of strains.

In some conditions, it is advantageous to combine two or more non-toxigenic strains that have complementary spectrums of prevention in order to achieve prevention of disease against a broader range of toxigenic C. difficile organisms. This strategy is based on the assumption that the two or more strains each colonize effectively when administered together and at the same time (so that neither strain has the advantage of being the first to arrive in the GI tract). Equivalent amounts of each type in the combination are a starting point for administration to prevent any one type from having an advantage in numbers. Ratios are adjusted if initial amounts are not effective.

It is possible to genetically engineer non-toxigenic strains of C. difficile by removing or manipulating the two genes responsible for production of the C. difficile toxins, A and B, so as to create strains that no longer produce the toxins responsible for causing C. difficile-associated disease (CDAD). Such strains are suitable for the practice of the present invention to prevent CDAD in the same manner as naturally non-toxigenic strains are disclosed herein. Such strains would have to undergo extensive safety and efficacy trials in animals and humans to assure that they were safe, e.g. had not acquired any inadvertent virulence properties as a result of genetic engineering. They would also have to be shown to be efficacious as a preventive measure by the methods disclosed herein, and to not revert back to their original toxigenic state or reacquire the toxin genes.

The methods and compositions of the present invention are useful to prevent and treat disease in humans or non-human animals, and are particularly useful for preventing and treating multiple relapses.

BRIEF DESCRIPTION OF THE DRAWINGS

FIG. 3: is agarose gel photographs of REA band patterns of types S1, M3, M4, M23, T7, J9, and VPI 2018.

DETAILED DESCRIPTION OF THE PREFERRED EMBODIMENT

Figure 1:
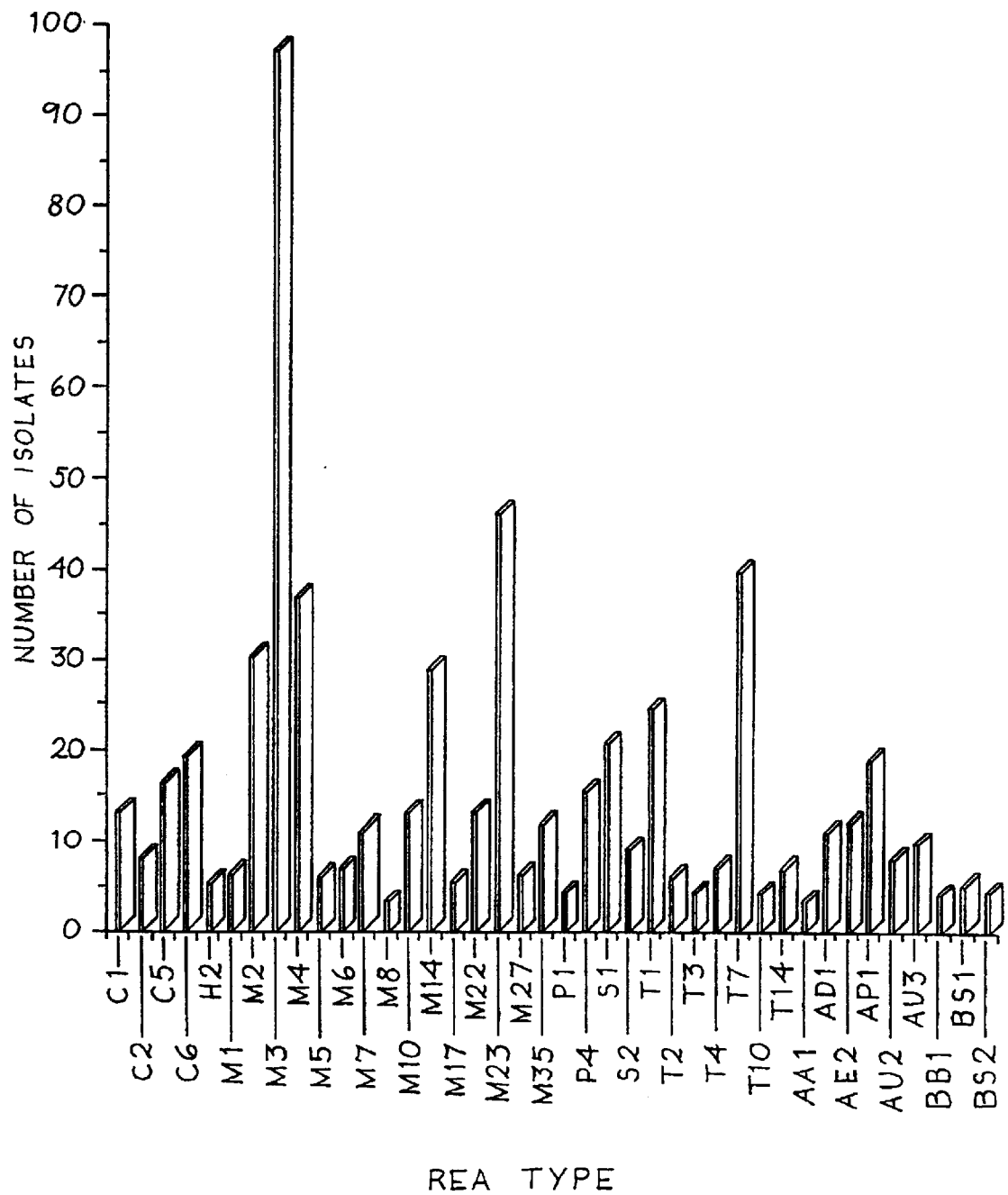
FIG. 1: illustrates the frequency of isolation of non-toxigenic C. difficile REA types for which more than 3 isolates were recovered. Strains were obtained from patients and the environment of multiple U.S. hospitals and chronic care facilities, but mainly the Minneapolis VA. Medical Center.

The invention provides methods and compositions for preventing and treating C. difficile-associated diseases (CDAD) in humans and non-human animals, e.g. mammals and birds. Prevention is used herein to mean that the risk of developing CMAD is reduced by approximately 80% or more compared to comparably exposed animals or humans in the same environment. Prevention is achieved by administering prophylactically a non-toxigenic strain or combination of strains of C. difficile to a subject at risk. A subject at risk is one who has received antimicrobial or antineoplastic agents having antimicrobial activity, and is in a high-risk environment such as a hospital or nursing home for humans; or a flock or herd of animals where disease due to C. difficile is occurring or likely to occur due to administration of antibiotics.

The usual presentation of CDAD includes the presence of: (1) diarrhea, defined by a variety of criteria (e.g., at least six watery stools over 36 hours, three unformed stools in 24 hours or 2 days, or eight unformed stools over 48 hours); (2) pseudomembranes seen at lower gastrointestinal endoscopy, or toxin A or B from C. difficile detected in the stool, or a stool culture positive for the presence of a toxin-producing C. difficile; and (3) no other recognized etiology for the diarrhea. (Gerding, 1995)

Non-toxigenic Strains of C. Difficile

A method of the invention comprises administering to a subject a non-toxigenic strain of C. difficile preferably a strain selected from one or more of the M, T, C, P, S and AP groups. For example, the M group is a group of C. difficile strains identified by restriction endonuclease analysis (REA) of the total genomic DNA of approximately 4000 C. difficile isolates. Most of the isolates were obtained from patients and environmental sources at the Minneapolis Veterans Affairs Medical Center over a period of ten years. The remaining isolates were obtained from various other hospitals. The method in which the REA typing of these isolates was performed is described in Clabots et al. (1993).

The C. difficile isolates were classified into groups on the basis of DNA restriction band pattern similarity on agarose gels. Briefly, the first isolate with a new DNA band pattern was arbitrarily designated as a reference REA type. Similarities between new and reference REA types were scored by visual comparison of each 1-mm segment of the top 60 mm of the DNA band patterns run on the same gel. A similarity index (SI) was calculated as the number of identical segments expressed as a percentage of the total segments. Any new REA type with an SI of ≧90% compared with an existing reference REA type was included in that group and given a specific type designation, for example, in the "M" group, types are designated as M1, M2, M3 ... M23 ... M35. Any new REA type with an SI of <90% was designated the primary reference REA type for a new group and was used for future group comparisons. The groups were designated by letters, and distinct REA types within a group were designated by arabic numbers.

The group arbitrarily designated "M." contains the largest number of isolates (347 of the 4000 toxigenic and non-toxigenic isolates typed so far), wherein "isolates" means an independently obtained specimen of the organism. Therefore, this group is a candidate for use in the present invention. The members of the M group are closely related, with an SI of over 90% by definition. The M group contains 35 distinct REA types (members of an REA type have an SI of 100%), with M3 and M23 being the most prevalent REA types. All isolates of the M group are non-toxigenic. The size of the group is not limited to 35 because new M types are identified from time to time.

Strains M3 and M23 are particularly preferred strains for use in the invention. They have been found to prevent CDAD in 95–100% of hamsters challenged acutely with toxigenic strains of *C. difficile* known to be highly virulent in humans and 100% fatal in hamsters (see Example 1). The M strains are more protective in hamsters than previously tested strains, for which survival only improved by 72% (Wilson and Sheagren, 1983, Boriello and Barclay, 1985), and was not as durable as with M strains. M3 prevents CDAD for at least 60 days after its administration, and M3-treated animals remain disease free for at least 100 days after challenge with highly virulent toxigenic strains (see Example 1). The very high level of protection and the fact that the protection is extremely durable were not to be expected in view of the results reported in the prior art.

Groups are stored at the VA Lakeside Medical Center, 333 East Huron, Chicago, Ill. 60611 as a library of more than 75 distinct *C. difficile* REA groups including the M, B, J, C, AP, P, S, and T groups.

Although not wishing to be committed to any particular theory, it is hypothesized that the ability of a non-toxigenic strain to protect against CDAD correlates with its ability to colonize the gut. In turn, the most frequently isolated REA types from humans are believed to be the best at colonizing the human gut. To select a strain or combination of strains for a particular animal, for example, the procedure illustrated in FIG. 1 of isolating and typing non-toxigenic strains is followed and the most frequent isolates found in that species are selected for efficacy trials as described herein. Alternatively, the same non-toxigenic types found in humans (FIG. 1) are suitable for use in animals as well (see examples for hamster data). Thus, other closely-related members of the M group and other frequently isolated non-toxigenic groups (e.g., the T group) and REA types (e.g., T1 and T7) are suitable candidates. See FIG. 1 which illustrates the frequency of isolation of non-toxigenic *C. difficile* REA types for which more than 3 isolates were found.

Strains of *C. difficile* useful in the invention are cultured and identified as *C. difficile* by standard microbiological methods well known in the art. For suitable techniques, see Clabots et al., (1993) and Kristjansson et al. (1994). *C. difficile* concentration is measured in colony forming units (cfu), as is well known in the art.

Figure 2:
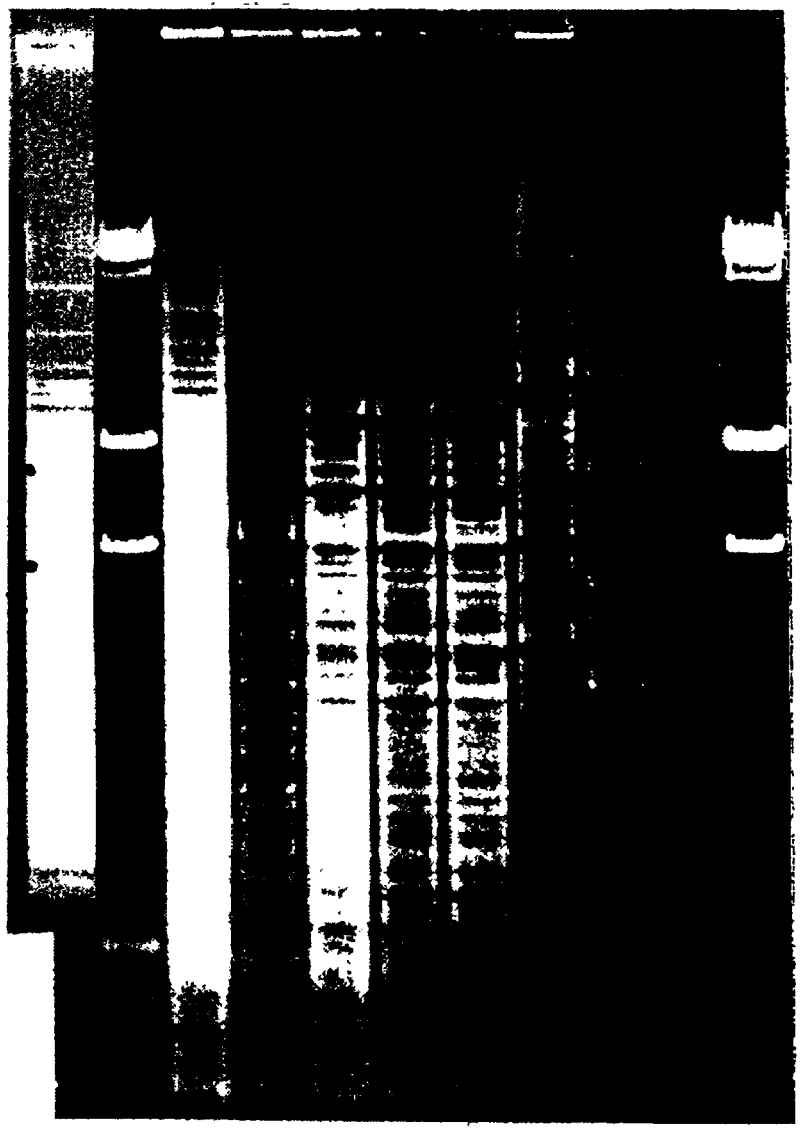
FIG. 2: is a photograph of REA band patterns on an agarose gel for C. difficile strains M1 (the reference isolate for the M group), M3, M23, M4, M2, and M14. Strains VPI 2018 (Wilson and Sheagren, 1983) and toxigenic strain REA type J9 are included for comparison.

Strains of *C. difficile* useful in the invention are further identified by REA typing as described in Clabots et al. (1993). By use of the M1 reference isolate, other members of the M group can be identified. FIG. 2 shows representative agarose gels of Hind III-restricted DNA from *Clostridium difficile* strain type M1 (reference strain for the M group), and strains M3, M23,t M4, M2, M14 (the most frequently isolated M types in descending order of frequency of isolation), strain VPI 2018 used by Wilson and Sheagren and not an M group strain, and strain type J9, a toxigenic *C. difficile* strain shown for comparison. Molecular weight markers of lambda DNA restricted with Hind III are shown on the left and right lanes of the gel. Lambda molecular weight marker locations for the M1 gel are indicated by black dots. FIG. 3 is similar to FIG. 2 in showing gels of M3, M4, M23, J9 and VPI 2018, and in addition shows two other non-toxigenic types, T7 and S1. By use of an M3 or other M type isolates, other M3 isolates can be identified by their identical restriction endonuclease band pattern or DNA fingerprint. Similar procedures are followed for the other groups.

Target Subjects for Prevention and/or Treatment

Subjects at risk for CDAD include humans and animals receiving antibiotics or antineoplastic drugs, especially the elderly and those who are hospitalized for prolonged periods of time or institutionalized.

Strains of *C. difficile* from the M group are suitable for practice of the invention, because of their ability to colonize well. Such strains are also useful for therapeutic purposes to treat patients who have had relapses of *C. difficile* diarrhea following treatment with antibiotics such as vancomycin or metronidazole. Such patients are exceedingly difficult to cure and are preferred choices for administration of the non-toxigenic strains. Such therapy is preferably administered after first treating the patient with vancomycin or metronidazole to reduce the population of toxigenic *C. difficile* and to control diarrhea. The vancomycin or metronidazole is stopped for 12–24 hr, and then the non-toxigenic strain of *C. difficile* is administered orally in the same manner as described for the preventive use of the strain. Repeated doses or higher doses of non-toxigenic *C. difficile* may be required for treatment as compared to prevention of CDAD. Strains M, T, C, AP, P, S and combinations thereof are suitable M strains of *C. difficile* are preferred for treatment of relapses because of the known high rate of colonization by M strains in humans, and the low rate of *C. difficile* disease in humans colonized by non-toxigenic strains of *C. difficile*.

Use of the M strains for prevention or treatment of animals is also suitable, particularly in the horse and chinchilla industry where disease is common and frequently fatal. Use of the M strains in animals for prevention or treatment of *C. difficile* disease is also within the scope of the invention.

Method of Administering Non-toxigenic *C. Difficile*

For prevention, non-toxigenic strain of *C. difficile* is administered to the subject prior to the patient's developing CDAD. For instance, the non-toxigenic strain of *C. difficile* is administered shortly after the patient begins to receive antibiotics, especially if other patients in the same facility have developed CDAD. The timing of administration to patients who have received antibiotics is critical. Colonization is unlikely to occur if antibiotics have not been given, because the normal bacterial flora of the gastrointestinal (GI) tract will prevent colonization. However, after antibiotics are administered, alterations in GI tract flora permit colonization. Generally, protective colonization should be accomplished within 24–72 hours of antibiotic initiation in order to achieve protection before exposure to toxigenic strains occurs. However, the non-toxigenic strain may be administered at any time following initiation of antibiotic treatment.

The non-toxigenic strains of *C. difficile* are administered orally or enterally to a subject via, e.g. a nasogastric or gastric tube. Effective dosage forms and dosage amounts effective to prevent CDAD may be determined empirically, and making such determinations is within the skill of the art. It is understood by those skilled in the art that the dosage amount will vary with the particular M or other group strain used, as disclosed herein, the patient's status (including illnesses being treated, age and size), other drugs including antibiotics being administered to the patient, and other factors well known in the medical art to affect dosage. Amounts and numbers of doses required for successful treatment may be higher than required for prevention.

A dosage of non-toxigenic *C. difficile* is selected that is sufficiently high to colonize the GI tract of the recipient, for example, $10^4$ to $10^6$ cfu per kg of body weight are suitable. Exact dosages required in humans are refined by studies in normal human volunteers. Multiple doses or larger doses may be required for certain strains and in certain situations such as when the patient is receiving ongoing antimicrobials (because the antimicrobial being given may inhibit or kill the *C. difficile* being given).

Exemplary dosages are those within the range of from about $10^4$ to about $10^8$ cfu per kg, preferably $10^4$ to about $10^6$ cfu per kg. Higher doses or repeated administration may be required if colonization is not established with the first dose administered. A single dose is expected to establish colonization, but the concomitant administration of certain antimicrobials to which the non-toxigenic *C. difficile* is susceptible may require administration of additional doses.

Preferably the non-toxigenic strain is administered as a pharmaceutical composition comprising the non-toxigenic strain of *C. difficile* in combination with a pharmaceutically-acceptable carrier. Each carrier must be "acceptable" in the sense of being compatible with the non-toxigenic strain, such as saline or glucose solution, should also not be injurious to the patient and should not kill or inhibit growth of the micro-organisms in the composition.

The amount of the strain that will be combined with a carrier to produce a unit dosage form will vary depending upon the factors described above. The amount will generally be that amount which is the lowest dose effective to produce colonization and a preventive or therapeutic effect. Such determination is made by conducting trials in normal volunteers who first receive an antimicrobial such as clindamycin followed at 24–48h by the oral non-toxigenic *C. difficile* strain to be tested.

Methods of preparing pharmaceutical formulations or compositions are well known. They include the step of bringing into association the non-toxigenic strain with the carrier. Formulations of the invention suitable for oral administration include those in the form of capsules, cachets, pills, tablets, powders, granules, or a suspension in an aqueous liquid, each containing a predetermined amount of a strain either as vegetative cells or spores. Spores are the preferred state of the organism for administration because they survive drying, lyophilization and exposure to air. Methods to prepare spores of *C. difficile* include growth in a liquid or a solid medium to induce sporulation (Wilson et al., 1992). Quantitation of the number of spores present is determined by culture of 10-fold dilutions of the spore suspension under anaerobic incubation conditions.

Either lyophilized spores in a capsule or a liquid dosage form is used. In addition to the group strain, the liquid dosage form may contain inert carriers, commonly used in the art, such as, for example, water, buffers or other aqueous solvents. Besides inert diluents, the liquid dosage form can also include adjuvants such as suspending, sweetening, flavoring, and coloring agents. [e.g a glucose solution, fructose solution.] It may also be desirable to include isotonic agents, such as sugars, sodium chloride, and the like in the liquid dosage form. Another preferred dosage form is a powder or granules which can be reconstituted into a liquid dosage form just prior to use by the addition of water or a similar diluent.

The formulations are suitably presented in unit-dose or multi-dose sealed containers, for example, ampoules and vials. The formulations may be stored in a lyophilized condition and be administered with the addition of the sterile liquid carrier, for example water for injection, immediately prior to use. The lyophilized formulations may also be administered in capsule form without the use of a liquid carrier. Extemporaneous suspensions may be prepared from sterile powders, granules and tablets.

For clinical use, continued studies in hamsters are used to rank the efficacy of strains and combinations of strains including tests of the duration of prevention, and efficacy when antimicrobial use is continued.

Human volunteers will be administered an antimicrobial followed by non-toxigenic *C. difficile* to determine if the gastrointestinal tracts of the volunteers become colonized, the dosage required to do so, the duration of colonization, and the safety/side effects of colonization. If these studies show that the volunteers are safely colonized for a sufficient period of time (probably one or more months), then a strain or combination of strains will be selected for a prevention trial in patients.

The prevention trial in patients will be conducted at multiple hospitals where patients who are beginning antibiotic treatment will be asked to participate in a double-blinded, placebo-controlled trial to determine if *C. difficile* disease can be prevented by colonizing the patients with non-toxigenic *C. difficile*. Hospitals will be selected that have high rates of CDAD in their institutions. End points will be 1) number of CDAD cases in treated versus placebo patients, 2) success in colonizing patients with non-toxigenic *C. difficile*, 3) adverse or side effects in treated vs placebo patients.

EXAMPLES

The following examples are presented for illustrative purposes and do not limit the invention.

Example 1

Using Strain M3 to Prevent CDAD in Hamsters

A. Establishing CDAD in the Hamster

The Syrian hamster model is by far the most frequently used and best described model of CDAD in an animal. It is considered predictive of results in humans, although the disease is more severe and more often fatal in hamsters than in humans. (Onderdonk, 1988)

Specific-pathogen free 80–120 g Syrian hamsters were purchased from Sasco, Inc., Omaha, Neb. and housed in individual isolator cages fitted with air filters on their lids and wire mesh floors to minimize coprophagia. Cages, food, water bottles, water, and bedding were autoclaved in sealed bags prior to use to minimize contamination of the animals by environmental spores of C. difficle. Personnel handling animals wore sterile gloves to minimize contamination. All animals had fecal pellets cultured on taurocholate-cefoxitin-cycloserine-fructose-agar (TCCFA) selective for C. difficile prior to study to assure that they were free of the organism.

Clindamycin was administered to groups of ten of the hamsters by oral gavage needle at a dose of 30 mg/kg. Five days after receiving the antibiotic, the hamsters were given spore preparations of toxigenic C. difficile B1 or J9 by oral gavage. The spore preparations were prepared according to the method of Wilson 1982 and 1983, but were administered in a single aliquot of 100 cfu per animal. This dose had previously been determined to be lethal in dose-ranging studies.

The toxigenic strains used were REA types B1 and J9, identified by their distinct restriction endonuclease pattern. (Clabots et al., 1993). These two strains were chosen because they cause epidemics of CDAD in human patients in hospitals. These strains are highly virulent, producing CDAD in nearly 50% of the patients from whom they were isolated.

Diarrhea and mortality were monitored, and feces were cultured using TCCFA medium. All 20 of the hamsters receiving either of the two toxigenic C. difficile strains developed stools that were culture-positive for the challenge organism by 24 hours post-inoculation, and all of the animals developed "wet-tail" (diarrhea) and died within 48 hours of inoculation (100% mortality at 48 hours). Postmortem examination showed marked colitis and cecitis with large dilated cecum and hemorrhagic fluid (the colon and cecum are the site of CDAD in hamsters).

B. Pretreatment of Hamster with M3 to Prevent CDAD caused by B1

Non-toxigenic REA type M3 was administered by oral gavage to a group of 10 hamsters 48 hours after treatment with clindamycin as described above in section A. The oral inoculum was a spore preparation (prepared as described in section A) containing a large number of spores ($5\times10^5$ to $10^6$ cfu per animal) in order to achieve colonization with a single dose.

Feces were cultured using TCCFA medium. All hamsters had high counts of M3 in fecal pellets by 28 to 72 hours post inoculation with the spores.

Animals were then challenged on day 5 following the clindamycin treatment (3 days after administration of M3) with 100 cfu per animal of toxigenic B1 by oral gavage as described in Section A. Diarrhea and mortality were followed for 30 days and compared with the same outcome data from the previously studied unprotected animals (see section A). Feces were cultured using TCCFA medium on days 1, 2, and 3 following challenge with the toxigenic isolate, and weekly thereafter. Selective medium containing erythromycin was used to differentiate the mix of toxigenic challenge organism (resistant to erythromycin) and non-toxigenic protective organisms (sensitive to erythromycin) over time.

Animals that survived acute challenge at 30 days were observed for an additional 69 days to see if any delayed disease due to the toxigenic organism occurred. Weekly fecal cultures were continued to determine if colonization with the non-toxigenic isolate persisted.

All 10 hamsters given M3 remained well (diarrhea free) for the entire period of follow-up which ranged from 63 to 99 days. Animals were sacrificed beginning at day 63 through day 99 at intervals, and postmortem examination revealed no evidence of disease in the colon or cecum. The animals had detectable M3 in feces for a mean of 65 days (range of 4–92 days).

C. Pretreatment of Hamsters with M3 to Prevent CDAD cause by J9

Twelve hamsters were given clindamycin, 30 mg/kg, by oral gavage as described in section A. Two days later, 10 hamsters were given $6.5\times10^5$ cfu per animal of M3 C. difficile spores by oral gavage as described in Section B. Two hamsters served as untreated controls, that is, they were not given M3.

Feces were cultured using TCCFA medium. Nine of the ten hamsters receiving M3 had high counts of M3 in fecal pellets by 28 to 72 hours post inoculation of the spores. The tenth hamster that received M3 and the two controls (not given MB) did not have M3 detected in fecal pellets.

Three days after M3 administration (five days after administration of clindamycin), all 12 hamsters were given 500 cfu of spores of C. difficile toxigenic strain J9 by oral gavage as described in Section A. Diarrhea and mortality were monitored for 30 days and compared with the same outcome data from the previously studied unprotected animals (see section A). Feces were cultured using TCCFA medium on days 1, 2, and 3 following challenge with the toxigenic isolate, and weekly thereafter. Selective medium containing erythromycin was used to differentiate the mix of toxigenic challenge organisms (resistant to erythromycin) and non-toxigenic protective organisms (sensitive to erythromycin) over time.

Animals that survived acute challenge at 30 days were observed for an additional 23 days to see if any delayed disease due to the toxigenic organism occurred. Weekly fecal cultures were continued to determine if colonization with the non-toxigenic isolate persisted.

Nine of the ten hamsters that received ME remained well (that is diarrhea free) for the entire period of follow-up, which was 53 days. Weekly stool cultures showed strain M3 in fecal pellets for 56 days (after M3) in 8 of the 9 animals and for 32 days in the ninth animal. Strain J9 was not found in the stools of the animals. The nine hamsters were sacrificed at day 53 (56 days after administration of M3), and postmortem examination showed no evidence of colon or cecal disease.

The two control hamsters that did not receive strain M3 and the hamster that received M3, but did not have it detected in stool pellets, that is, showed no evidence of colonization, died within 30–48 hours of J9 inoculation and had strain J9 recovered from stools within 4–29 hours of inoculation. Postmortem examination showed marked dilation of the cecum, cecitis, colitis and large amounts of bloody cecal fluid.

Thus, protection was effective in 9 of 10 hamsters that received C. difficile strain M3. The animal that failed to be protected did not have detectable amounts of M3 in stool pellets at the time of challenge with the toxigenic J9 strain, whereas the other nine hamsters had detectable M3.

D. Safety and Durability of Prevention by M3

Twelve Syrian hamsters had stool pellets cultured for C. difficile and were shown to be free of the organism. Five days later they were given 30 mg/kg of clindamycin by oral gavage as described in section A. Two days later they were given 0.5–1.0×10⁶ cfu of spores of *C. difficile* strain M3 per animal by oral gavage as described in Section B.

All animals demonstrated high counts of *C. difficile* strain M3 in their stools by 24 to 77 hours after inoculation. Fecal pellets from each hamster were cultured weekly thereafter to document persistence of colonization. Stools remained positive for strain M3 for 28 to 84 days post inoculation.

Mortality and diarrhea were followed as measures of the safety of strain M3. All animals remained well. Four animals were sacrificed for pathologic examination 60 days after receiving M3. This examination demonstrated no abnormalities in the colon or cecum.

Fifty-four days after receiving M3, three hamsters were challenged with 100 cfu per animal of toxigenic strain J9 by oral gavage as described in Section C. These animals remained well for 30 days and developed no ill effects from the J9 challenge. Fecal pellets remained positive for M3 in 2 of the 3 animals for the full observation period, and for 42 days in the remaining animal.

The remaining five hamsters were challenged 60 days after receiving the protective strain M3 with 100 cfu per animal of toxigenic *C. difficile* strain B1 by oral gavage as described in Section B. Although M3 could no longer be detected in the stool pellets of these animals, they remained well and developed no ill-effects as a result of the B1 challenge. The hamsters were followed for an additional 92–100 days following B1 challenge and developed no evidence of illness. At postmortem examination, there was no evidence of cecitis or colitis. M3 was isolated from the cecum of one animal 159 days after M3 inoculation, which was 117 days after the last positive fecal pellet culture for M3.

Thus, the protection afforded by M3 is extremely durable, as the hamsters were completely protected from challenge with highly virulent toxigenic strains B1 and J9 for 54–60 days after becoming colonized with strain M3.

E. Absence of Virulence Genes in M3

The production of toxin A and probably the production of toxin B (the two toxins are almost invariably present together) are the most important virulence factors in *C. difficile*. (Barriello et al., 1990; Lyerly et al., 1988). Strain M3 was tested to determine if it produced toxins A and B or contained the genes for these two toxins.

The standard HEp-2 cell cytocoxicity assay was used to assay for toxin B in supernatant of cultures of M3 grown in chopped meat medium (CMM) as described in Johnson et al. (1990). M3 was found to be noncytotoxic, indicating the absence of Toxin B.

Supernatants of M3 cultures grown in CMM at 37° C. for 7 days were also tested for toxin A by the use of a commercial ELISA assay (TOX-A TEST, Techlab, Blacksburg, Va.). M3 was found not to produce Toxin A.

Southern hybridization was used to determine if the genes coding for toxins A and B were present in M3. A modification of the transfer techniques described by Southern (1975) was used to perform this analysis. In brief, DNA from *C. difficile* M3 was extracted, purified, HindIII-digested, and separated by agarose gel electrophoresis as described in Clabots et al., (1993). Following electrophoresis, the DNA was hydrolyzed by acid depurination, denatured in alkaline buffer, then neutralized. The DNA was then transferred to a Zetabind synthetic membrane filter (AMF-Cuno, Meriden, Conn.) by capillary transfer in a high salt solution, the filter rinsed in low salt buffer, and dried at 80° C. Toxin A and toxin B gene sequences were assayed using oligonucleotide DNA probes derived from the published sequences of each gene (Barroso et al., 1990; Dove et al., 1990). A 19-mer oligonucleotide probe from the toxin A gene sequence that is repeated 5 times near the 3' end and a 20-mer sequence from position 503 near the 51 end of the toxin B gene were used to probe M3. Also, an extensive set of toxin A and toxin B probes obtained from restriction digests of cloned toxin A and B genes were used. The probes were labelled with ³²P-deoxycytidine triphosphate by random priming, then hybridized to the DNA fixed to the filter using the methods of Sambrook et al. (1989). The hybridized bands were then visualized by autoradiography.

None of the probes for toxin A and toxin B genes showed hybridization. Thus, M3 was found to contain neither the gene for toxin A nor the gene for toxin B.

The phenotypic and genotypic evidence indicates M3 does not produce toxins A and B and does not contain the genes coding for these two toxins. The absence of these virulence factors provides further confirmation that the administration of M3 to human patients is safe.

Example 2

Use of M23 to Prevent CDAD in Hamsters

A. Pretreatment with M23 to Prevent CDAD caused by B1

An REA type M isolate, M23, the second most frequently isolated M type found in a survey of asymptomatic patients who carried *C. difficile* in their stools, was used to generate the following data. Non-toxigenic REA type M23 was administered by oral gavage at a dose of 10⁶ cfu of spores to 10 Syrian Golden Hamsters 48 hours after treatment with clindamycin as described in Example 1, section A. Two hamsters that received clindamycin were not given M23 and served as unprotected controls.

Feces were cultured using TCCFA medium. All 10 hamsters that received M23 spores had *C. difficile* strain M23 detected in feces 50 to 72 hours after gavage administration. The two control hamsters had no *C. difficile* detected in feces.

Hamsters were then challenged on day 5 following the clindamycin treatment (3 days after administration of M23) with 100 cfu per animal of toxigenic strain B1 of *C. difficile* by oral gavage as described in Section B of Example 1. Diarrhea and mortality were monitored for a minimum of 28 days following B1 for all surviving animals. Feces were cultured using TCCFA medium on days 1, 2, 3 and weekly following challenge with the toxigenic isolate B1. As in Example 1, selective medium containing erythromycin was used to differentiate the mix of toxigenic challenge organisms (resistant to erythromycin) from the non-toxigenic protective organisms (sensitive to erythromycin) over time.

Animals that survived acute challenge for at least 28 days were sacrificed at a rate of two animals every one to two weeks out to a maximum of 65 days post B1 challenge, to observe for evidence of delayed disease or morphologic or histologic evidence of disease. Weekly fecal cultures were continued to determine if colonization with the non-toxigenic isolate persisted. All 10 hamsters given strain M23 remained free of diarrhea and survived for the entire period of observation (28 to 65 days) without evidence of disease. No evidence of disease was found in the colon or cecum of sacrificed animals. Strain M23 was detected in the feces of all 10 animals up to the time of sacrificed at day 28 to 65. Strain B1, the toxigenic challenge strain, was never detected in the feces of the animals that received M23.

In contrast, the two control hamsters that received clindamycin, but not strain M23, both had toxigenic strain B1 detected in feces within 24 hours of administration of strain B1, and died within 72 hours of administration of B1. Typical hemorrhagic cecitis was noted at post mortem examination.

B. Safety and Durability of Prevention by M23

Ten Syrian Golden Hamsters were administered strain M23, *C. difficile*, $10^6$ cfu per animal, by oral gavage, two days after pretreatment with oral clindamycin, 30 mg/kg by oral gavage as described in EXAMPLE 2, Section A. Two control animals received clindamycin, but did not receive strain M23.

All animals had fecal stool cultures performed using TCCFA media beginning 24 hours after M23 gavage and continuing weekly. All ten animals that received M23 had fecal cultures positive for the organism within 72–96 hours of receiving M23. All animals remained well and fecal cultures remained positive for 42 days in all animals with no evidence of adverse effects of colonization. Growth and weight gain were indistinguishable from control animals who also remained well and uncolonized.

All 12 hamsters were challenged with 100 ctu of toxigenic strain B1 spores at 41 days post clindamycin (39 days post M23 in 10 of the animals). All animals remained well and survived challenge with this virulent *C. difficile* isolate. The feces of all 10 animals colonized with M23 remained colonized with the organism. Control animals remained negative for any *C. difficile* in feces.

Since both control animals survived, it was unclear if the effect of clindamycin had waned, leaving the animals no longer susceptible to challenge with toxigenic *C. difficile*. To resolve this question, both control animals and five animals colonized with M23 were readministered clindamycin orally at a dose of 30 mg/kg 49 days following the original clindamycin (47 days after M23 administration). Five days after readministration of clindamycin, all seven hamsters were again challenged with 100 cfu of toxigenic strain B1 *C. difficile* spores. Both control animals were found to have B1 *C. difficile* in their feces within 24 hours of challenge, and died within 72 hours of challenge. Four of the five M23 colonized animals remained colonized with M23 and survived without apparent illness.

One M23 colonized animal was found to have B1 in fecal cultures and died 48 hours after challenge with strain B1. In summary, four of five (80%) of animals colonized with M23 were protected from rechallenge with toxigenic strain B1 after readministration of clindamycin. Two uncolonized control animals died from B5 infection. Post mortem examination showed typical hemorrhagic cecitis in all three animals that died. Surviving animals were sacrificed 10 days following B1 challenge and showed no evidence of cecitis or colitis at postmortem examination.

As was strain M3 and all types of the M REA group, strain M23 was found to be non-cytotoxic in the standard HEp-2 cell cytotoxicity assay and did not react in the TOX-A TEST for Toxin A (TOX-A TEST, TechLab, Blacksburg, Va.). Molecular probing of M23 for the toxin A and toxin B genes was also negative.

For clinical use, continued studies in hamsters are used to rank the efficacy of strains and combinations of strains including tests of the duration of prevention, and efficacy when antimicrobial use is continued.

Example 3

Genetically Engineered Non-toxigenic Strains of C. Difficile

A genetically engineered strains of non-toxigenic *C. difficile* are prepared by A. selecting a toxigenic strain of *C. difficile*; B. deleting the genes that encode toxin A and toxin B, said deleting achieved by means of recombinant genetic methods. (The toxin A and B genes are identified and cloned).

DOCUMENTS CITED

Barroso et al., *Nucleic Acids Res.*, 18, 4004 (1990)
Borriello et al., *Rev. Infect. Dis.*, 12, S185–191 (1990)
Borriello and Barclay, *J. Med. Microbiol.*, 19, 339–50 (1985)
Borriello, in *Anaerobes Today*, 195–202 (Hardie and Borriello eds. 1988)
Clabots et al., *J. Clin. Microbiol.*, 31, 1870–1875 (1993)
Corthier and Muller, *Infect. Immun.*, 56, 1500–1504 (1988)
Dove et al., *Infect. Immun.*, 58, 480–88 (1990)
Gerding et al, *Infect. Control. & Hospital Epidemiol.*, 16, 459–477 (1995)
Johnson et al., *The Lancet*, 336, 97–100 (1990)
Kristjansson et al., *J. Clin. Microbiol.*, 32, 1963–1969 (1994)
Lyerly et al., *Clin. Microbiol. Rev.*, 1, 1–18 (1988)
McFarland et al., *J. Amer. Med. Assoc.*, 271, 1913–1918 (1994)
Onderdonk, Chap. 7 In *Clostridium difficile*: Its Role in Intestinal Diseases, 115–125 (Rolfe and Finegold eds. 1988)
Sambrook, Fritsch and Maniatis, Molecular Cloning: *A Laboratory Manual* (2d ed. 1989)
Seal et al., *Eur. J. Clin. Microbiol.*, 6, 51–53 (1987)
Southern, *J. Mol. Biol.*, 98, 503 (1975)
Surawicz et al., Gastroenterology, 96, 981–988 (1989)
Tvede and Rask-Madsen, The Lancet, 1, 1156–1160 (1989)
Wilson and Sheagren, *J. Infect. Diseases*, 147, 733–36 (1983)
Wilson et al., *J. Clin. Micriobiol.*, 15, 443–46 (1982)

I claim:

1. A pharmaceutical composition comprising a pharmaceutically-acceptable carrier and at least one non-toxigenic strain of *C. difficile*, said strain not producing *C. difficile* toxins A and B and selected from the group consisting of M, M3, M23, T, T7, C, P, S, and AP as defined by restriction endonuclease analysis (REA) of the total genomic DNA of *C. difficile* isolates, on agarose gels.

2. The pharmaceutical composition of claim 1, wherein the non-toxigenic strains are selected from the group M and T.

3. The pharmaceutical composition of claim 2, wherein the non-toxigenic M strain is M23.

4. The pharmaceutical composition of claim 2, wherein the non-toxigenic T strain is T7.

5. The pharmaceutical composition of claim 2, wherein the non-toxigenic M strain is M3.

6. The pharmaceutical composition of claim 1, where the *C. difficile* is in the form of spores.

7. A pharmaceutical composition comprising a pharmaceutically-acceptable carrier and a combination of at least two non-toxigenic strains of *C. difficile* and not producing *C. difficile* toxins A and B and selected from the group consisting of M, M3, M23, T, T7, C, P, S, and AP as defined by restriction endonuclease analysis (REA) of the total genomic DNA of *C. difficile* isolates, on agarose gels.

8. The pharmaceutical composition of claim 7, wherein the *C. difficile* strains are administered in the form of spores.

9. A unit dosage form of a pharmaceutical composition comprising a non-toxigenic strain of *C. difficile* in a pharmaceutically-acceptable carrier said strains not producing *C. difficile* toxins A and B and selected from the group consisting of M, M3, M23, T, T7, C, P, S, and AP as defined by restriction endonuclease analysis (REA) of the total genomic DNA of *C. difficile* isolates, on agarose gels.

10. The unit dosage form of the pharmaceutical composition of claim 9, wherein the *C. difficile* strains are administered in the form of spores.

11. A method for preventing disease caused by *Clostridium difficile* in a subject treated with at least one antibiotic said method comprising establishing colonization by non-toxigenic *Clostridium difficile* of a gastrointestinal tract of the subject, by:

(a) obtaining at least one non-toxigenic strain of *C. dfficile*; said strain not producing toxins A or B and selected from the group consisting of M, M3, M23, T, T7, C, P, S and AP; and (b) administering to the subject within about 48 hours after the subject begins to receive antibiotics, an amount of at least one *C. difficile* strain sufficient to establish colonization within about 24–72 hours of administration of the non-toxigenic strain.

12. The method of claim 11, wherein the non-toxigenic strain is selected from the group consisting of the strains M, T, C, P, S and AP, said group classified on the basis of DNA restriction band similarities on agarose gels.

13. The method of claim 12, wherein the non-toxigenic strain is selected from the group M and T.

14. The method of claim 13, wherein the non-toxigenic M strain is M3.

15. The method of claim 13, wherein the non-toxigenic M strain is M23.

16. The method of claim 13, wherein the non-toxigenic T strain is T7.

17. The method of claim 11, wherein the *C. difficile* is administered in the form of spores.

18. The method of claim 11 wherein the *C. difficile* strain is administered as the composition of claim 1.

19. A method for preventing disease caused by *Clostridium difficile* in a subject treated with at least one antibiotic said method comprising establishing colonization by non-toxigenic *Clostridium difficile* of a gastrointestinal tract of the subject by:

(a) obtaining two or more non-toxigenic strains of *C. difficile* wherein the strains are selected from the group consisting of M, M3, M23, T, T7, C, P, S, and AP as defined by restriction endonuclease analysis (REA) of the total genomic DNA of *C. difficile* isolates, on agarose gels; and (b) administering to the subject an amount of the two or more *C. difficile* strains sufficient to establish colonization within two days of antibiotic administration.

20. The method of claim 19, wherein the *C. difficile* strains are administered in the form of spores.

21. The method of claim 19, wherein the *C. difficile* strains are administered as the composition of claim 7.

22. A method for treating a subject having a disease caused by toxigenic *Clostridium difficile*, said method comprising administering first an antibiotic followed within about 24 hours after antibiotics are stopped by a dose of at least one non-toxigenic strain of *C. difficile*, that is effective to reduce or suppress regrowth of the population of toxigenic *C. difficile* in the gastrointestinal tract of the subject and to control diarrhea in the subject said method comprising:

(a) obtaining at least one non-toxigenic strain of *C. difficile* wherein the strain is selected from the group consisting of M, M3, M23, T, T7, C, P, S, and AP; and (b) administering to the subject an amount of the at least one non-toxigenic *C. difficile* strain sufficient to establish colonization within about 24–72 hours after administration of the non-toxigenic strain.

23. The method of claim 22, wherein the strain is selected from the group consisting of M, T, C, P, S and AP said group classified on the basis of DNA restriction band similarities on agarose gels, and not producing *C. difficle* toxins A and B.

24. The method of claim 22, wherein the antibiotic is metronidazole or vancomycin.

25. The method of claim 22, wherein the non-toxigenic strain is selected from the group consisting of M and T.

26. The method of claim 22, wherein the *C. difficile* is administered as spores.

27. The method of claim 22, wherein the dose of at least one non-toxigenic strain of *C. difficile* is administered as the composition of claim 1.

28. A method to prevent relapse of *C. difficile* disease caused by toxigenic *C. difficile*, said method comprising administering first an antibiotic followed by administering an effective dose of at least one non-toxigenic *C. difficile* strain within about 24 hours after the antibiotic, said strains not producing *C. difficile* toxins A and B and selected from the group consisting of M, M3, M23, T, T7, C, P, S, and AP.

29. The method of claim 28, wherein the non-toxigenic *C. difficile* strain is selected from the group consisting of M, T, C, P, S and AP said group classified on the basis of DNA restriction band similarities on agarose gels.

30. The method of claim 29, wherein the strain is selected from the group consisting of the strains M and T.

31. The method of claim 30, wherein the M strain is M23.

32. The method of claim 30, wherein the T strain is T7.

33. The method of claim 28, wherein the *C. difficile* is administered in the form of spores.

34. The method of claim 28, wherein the *C. difficile* is administered as the pharmaceutical composition of claim 1.

35. The method of claim 28, wherein the *C. difficile* is administered as the pharmaceutical composition of claim 7.

36. The method of claim 28, wherein the antibiotic is metronidazole or vancomycin.

* * * * *